United States Patent [19]

Ohnuma et al.

[11] Patent Number: 5,271,418
[45] Date of Patent: Dec. 21, 1993

[54] BRACE FOR ANKLE JOINT

[75] Inventors: Noriyoshi Ohnuma, Funabashi; Daisaku Mukai, Tokyo; Hiroshi Ariga, Matsudo, all of Japan

[73] Assignee: Nippon Sigmax Co., Inc., Tokyo, Japan

[21] Appl. No.: 935,928

[22] Filed: Aug. 27, 1992

[30] Foreign Application Priority Data

Mar. 17, 1992 [JP] Japan .................. 4-014137[U]

[51] Int. Cl.⁵ ............................ A61F 5/37; A61F 5/00
[52] U.S. Cl. ...................................... 128/882; 602/23; 602/27
[58] Field of Search ............... 128/882; 602/5, 23, 602/24, 27, 28, 62, 65

[56] References Cited

U.S. PATENT DOCUMENTS

| | | |
|---|---|---|
| Re. 33,395 | 10/1990 | Peters .................. 602/27 |
| 1,381,290 | 6/1921 | Diadul ................. 602/27 |
| 4,517,968 | 5/1985 | Greene ................. 602/27 |
| 4,572,169 | 2/1986 | Mauldin ............... 602/27 |
| 4,665,904 | 5/1987 | Lerman ................ 602/27 |
| 4,719,926 | 1/1988 | Nelson ................. 602/27 |
| 5,069,202 | 12/1991 | Prock .................. 602/27 |
| 5,099,860 | 3/1992 | Amrein ................ 602/27 |

Primary Examiner—Michael A. Brown
Attorney, Agent, or Firm—Bacon & Thomas

[57] ABSTRACT

A brace for the ankle joint which comprises an outer cover for covering at least the ankle and a part of the lower leg, a pair of connection plates detachably attached to the inner surface of the outer cover at locations below the ankle by means of plane fasteners, and a pair of guard members which are to support the lower leg, and the lower ends of which are rotatably connected to the upper ends of the connection plates. The brace for the ankle joint is very safe, remarkably easy to use and provides an excellent fitness.

10 Claims, 3 Drawing Sheets

BRACE FOR ANKLE JOINT

BACKGROUND OF THE INVENTION

1. Field of the Invention

This invention relates to a brace for the ankle joint and, more particularly, to a brace which embraces the ankle joint for preventing damages of the ankle joint such as sprain, for treating the damages, and for preventing a recurrence of ankle joint troubles.

2. Background Art

A conventional brace for the ankle joint is provided with a pair of guard members which support the lower leg below the calf from the inner and outer sides, and a heel stirrup. The guard members are tightly fastened to join with each other with a strap provided at the calf portion.

When such a conventional brace is used, the guard members are exposed at the inner and outer sides of the lower leg. A problem therefore arises in that users themselves or other people may be injured by a contact with the exposed guard members. Since such danger is a serious problem in sport games, sport players have avoided using the conventional brace.

Further, since the conventional brace is designed to support the lower leg with the strap only, a whole-face tight contact is hardly obtained between the guard members and the leg. In other words, the conventional brace therefore lacks fitness upon use.

SUMMARY OF THE INVENTION

It is therefore an object of the present invention to provide an improved brace for the ankle joint which is very safe and which provides a comfortable fitness.

It is another object of the present invention to provide an improved brace of a supporter type for the ankle joint.

Briefly, a brace for the ankle joint according to this invention comprises an outer cover for covering at least the ankle joint and a part of the lower leg, a pair of connection plates detachably attached to the inner surface of the outer cover at locations below the ankle by means of plane fasteners such as Velcro ®, Magic Fastener ® or the like, and a pair of guard members which are to support the lower leg, and the lower ends of which are rotatably connected to the upper ends of the connection plates.

Since the guard members are not exposed outside, the brace for the ankle joint according to the present invention is very safe. The brace for the ankle joint according to the present invention is particularly suitable for sport players, because it does not hinder the movement of the ankle.

Further, the outer cover wholly covers and embraces the ankle joint together with the guard members, a sufficient fixing or supporting function can be obtained even when the guard members are designed to have a reduced thickness as compared to that of the conventional one. With this structure, the brace according to the present invention is easy to put on with comfortable fitness.

In a preferred embodiment, the brace is further provided with a strap, which tapes the heel in a shape of FIG. 8 (hereinafter referred to as a "strap for FIG. 8 taping". It provides an additional effect of preventing the talus from being pushed forward and out of position.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which.

PREFERRED EMBODIMENTS

Figure 1:
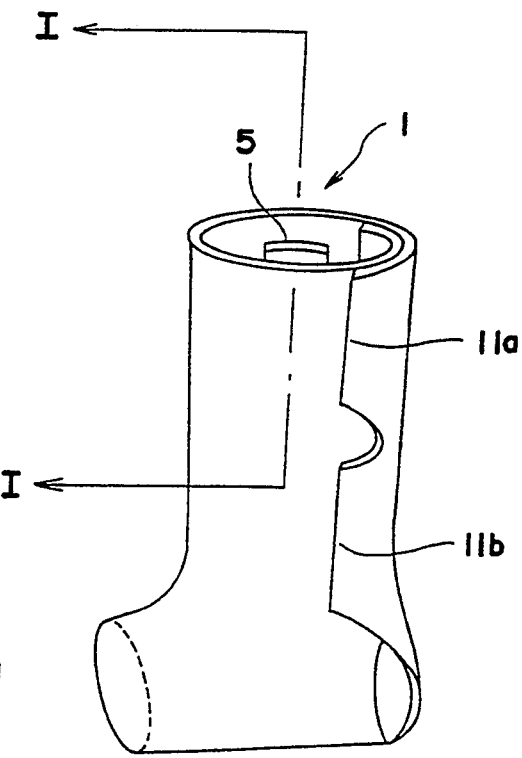
FIG. 1 is a perspective view of a brace for the ankle joint according to a preferred embodiment of the present invention.
Figure 2:
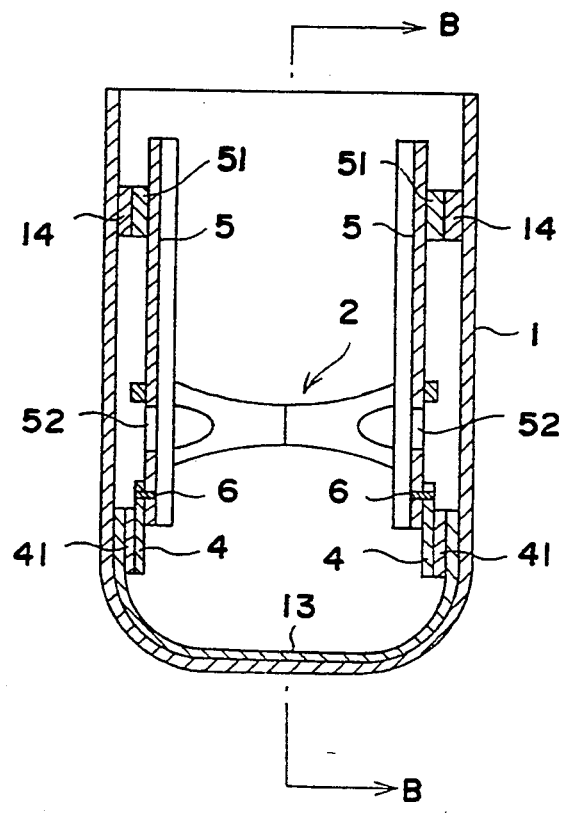
FIG. 2 is an enlarged cross section taken along line 1—1 in FIG. 1.
Figure 3:
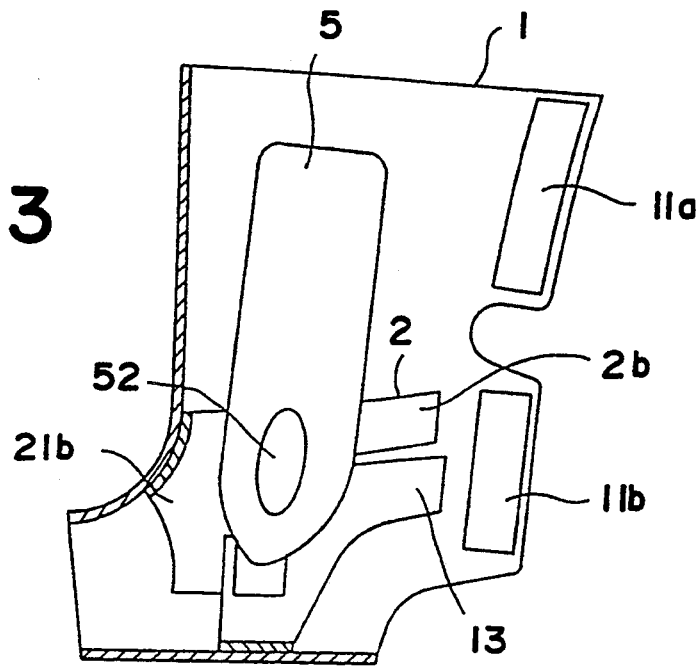
FIG. 3 is an enlarged cross section taken along line 11—11 in FIG 2.
Figure 4:
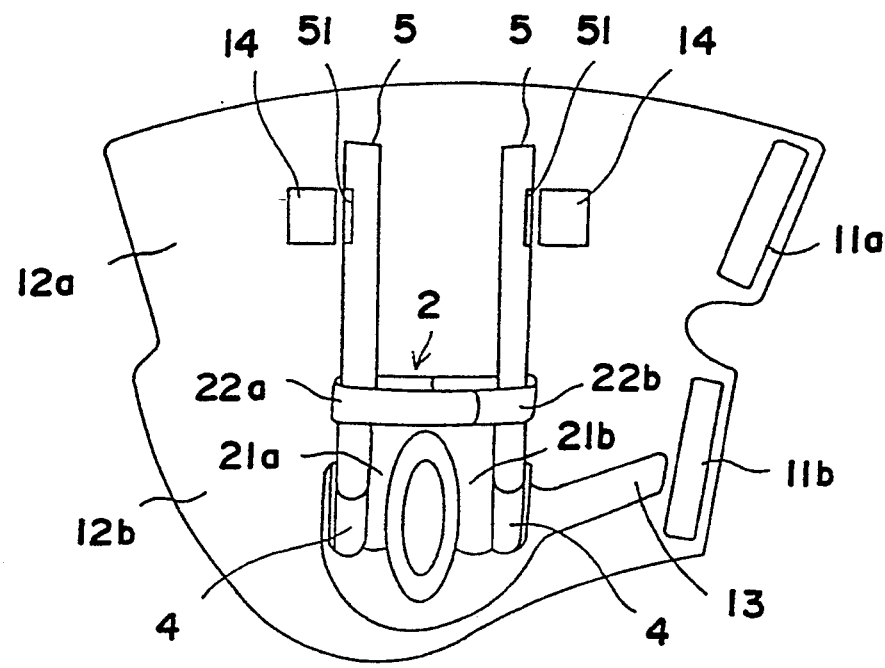
FIG. 4 is an unfolded view of the brace.
Figure 5:
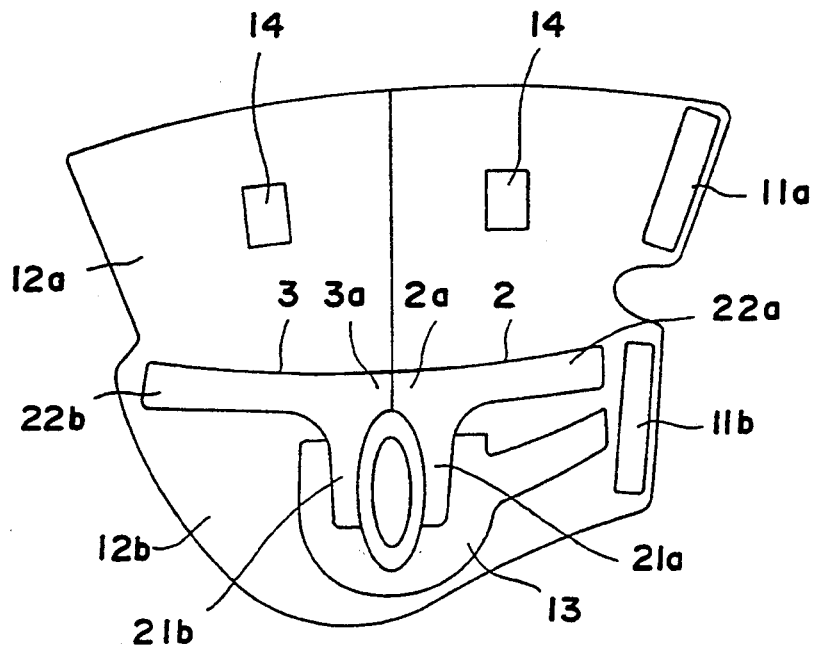
FIG. 5 is an unfolded view of the outer cover of the brace from which the guard members and connection plates have been detached.
Figure 6:
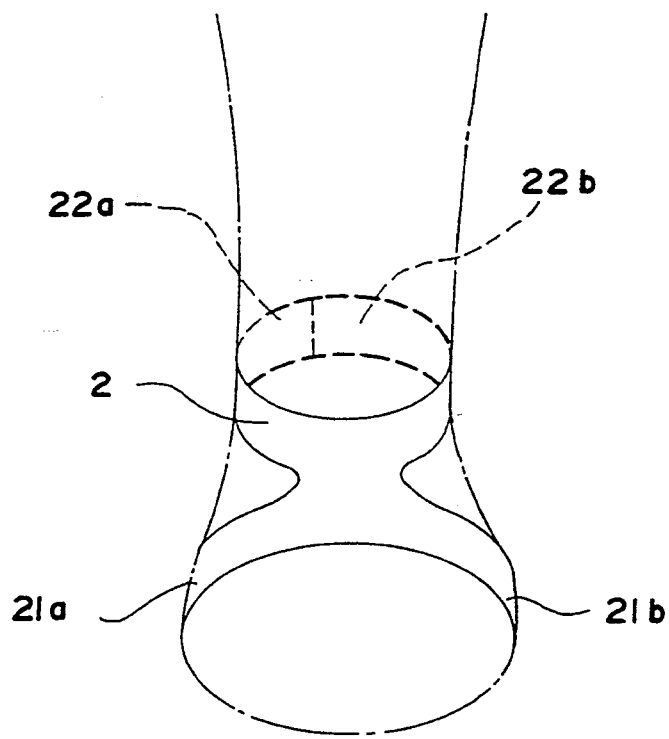
FIG. 6 is an illustration showing the shape of the strap for FIG. 8 taping when the brace is used.

The preferred embodiment of the present invention will now be explained with reference to the accompanying drawings.

In the drawings, reference numeral 1 denotes an outer cover for covering and supporting guard members 5 described later. Although the material of the outer cover 1 is not particularly limited, it is preferred to use a material having a shock-absorbing property and a proper elasticity.

The shape of the outer cover 1 is not particularly limited as long as it can completely cover the guard members 5. A preferred shape is a bootlike shape, as shown in FIG. 1. Its front end portion corresponding to the toes is cut away, and its back side portion is cut open in a vertical direction to form upper and lower fixation tabs 11a, 11b at one end, and upper and lower fixation tabs 12a, 12b at the other end, which are overlapped each other. The upper tabs 11a, 12a and lower tabs 11b, 12b are provided with plane fasteners to be detachably fastened to each other. This structure achieves an excellent capability of locking the heel (hereinafter referred to as "heel-lock capability") and easiness to wear.

Reference numeral 13 denotes a reinforcement portion for locking the heel, and it is constituted of an inelastic cloth overlaid on and affixed to the inner surface of the outer cover 1 by known fixation means such as sewing. The reinforcement portion 13 is so designed to tape and hold the heel portion in contact with a part of the sole slightly forward with respect to the heel, via a portion below the ankle to the Achilles tendon. This structure enhances the heel-lock capability of the outer cover 1, thereby providing a strong holding and supporting effect.

Reference numeral 14 denotes a pair of plane fastener elements which are provided on the upper portion of the inner surface of the outer cover 1. The plane fastener elements 14 are detachably coupled with plane fastener elements 51 provided on the upper portions of the outer surfaces of the guard members 5 for preventing the guard members 5 from getting out of position.

Reference numeral 2 denotes a strap for FIG. 8 taping, which is used for taping the heel in a shape of FIG. 8 and also for fastening the guard members 5. This strap for FIG. 8 taping is made of a single elastic belt having a shape of letter X. The lower ends 21a and 21b of the strap 2 are fixed to the inner surface of the outer cover 1, by fixation means such as sewing, at an area corresponding to the inner and outer sides of the foot and the instep of the foot. Further, the upper ends 22a and 22b of the strap 2 are detachably fastened to each other by means of a plane fastener.

The strap 2 may be constituted by a pair of straight straps, which are crossed each other to form a shape of letter X.

Reference numeral 4 denotes a pair of opposing connection plates detachably attached to the inner surface of the outer cover 1 at locations below the ankle by means of plane fasteners. Namely, plane fastener elements 41 are affixed to the outer surfaces of the connection plates 4, and the reinforcement portion 13 acts as plane fastener elements to which the plane fastener elements 41 are detachably attached. The area of the reinforcement portion 13 acting as the plane fastener elements is larger than the plane fastener elements 41. This allows users to adjust the position of the guard members 5 in accordance with the size of the foot or leg. Further, since the reinforcement portion 13 is used as the plane fastener elements, it is possible to make the manufacturing process simpler. The connection plates 4 are made of a material which is rigid or semi-rigid, such as plastics.

Although the reinforcement portion 13 is used as the plane fastener elements in this preferred embodiment, plane fastener elements may be affixed to the inner surface of the reinforcement portion 13 for coupling with the plane fastener elements 41. In this case, it is preferred that the plane fastener elements affixed to the reinforcement portion 13 be larger than the plane fastener elements 41.

The lower ends of the pair of guard members 5 are rotatably connected to the upper portions of the pair of connection plates 4, respectively, by means of shaft pins 6. The guard members 5 have a boardlike shape, and have curved inner surfaces corresponding to the shapes of the inner and outer sides of the lower leg portion below the calf. Each of the guard members 5 is formed with a cut-away hole 52 at a location corresponding to the ankle to obtain a perfect fitness between the guard members 5 and the lower leg.

The guard members 5 are made of a material which is rigid or semi-rigid, such as plastics. Further, it is preferred that the guard members 5 be provided with pads at their inner sides. This increases the safety of the brace.

Since the brace for the ankle joint according to the present invention has the above-mentioned structure, users can securely apply the brace to the ankle joint in a very easy manner, as easy as to wear a sock.

Further, since the guard members 5 are completely covered by the outer cover 1, and the outer cover 1 is in close and tight contact with the whole area of the lower leg portion to which the brace is applied, the brace according to the present invention is very safe avoiding possible dangers of hurting the user or other people by exposed guard members, and provides an excellent fitness.

Since the guard members 5 are not directly fixed to the outer cover 1, but are rotatably connected to thereon through the connection plates 4, the brace allows the up and down movement of the ankle. The brace is therefore particularly suitable for sport players.

Obviously, numerous modifications and variations of the present invention are possible in light of the above teachings. It is therefore to be understood that within the scope of the appended claims, the present invention may be practiced otherwise than as specifically described herein.

What is claimed is:

1. A brace for an ankle joint, comprising:
   a) an elastic outer cover having a first portion adapted to substantially cover the ankle joint and an adjacent part of a foot, a second portion adapted to wrap around and cover an adjacent part of a lower leg, and an inner surface;
   b) a pair of connection plates;
   c) first attaching means detachably attaching the pair of connection plates to the inner surface of said first portion of said outer cover at locations below the ankle joint;
   d) a pair of guard members adapted to support an adjacent portion of a lower leg; and
   e) pivot means pivotally attaching an end of each of the pair of guard members to a corresponding connecting plate, whereby the outer cover completely covers the pair of connection plates, the pair of guard members and the pivot means when the brace is applied to the ankle joint.

2. A brace for the ankle joint according to claim 1, further comprising:
   a) a strap for taping a heel adjacent to the ankle joint in a shape of a FIG. 8; and,
   b) second attaching means for attaching the strap to the inner surface of the outer cover.

3. A brace for the ankle joint according to claim 2, wherein said strap comprises:
   a) a single elastic belt having a generally "X" shape having upper and lower ends wherein the lower ends of said strap are fixed to the inner surface of said outer cover at locations corresponding to an area extending from inner and outer sides of an adjacent foot to an instep; and
   b) fastening means to detachably fasten the upper ends of said strap to each other.

4. A brace for the ankle joint according to claim 1, wherein said outer cover has a bootlike configuration with a toe part cut away, and further comprising:
   a) a pair of tabs adapted to be overlapped with each other; and
   b) fastening means to detachably fasten the pair of tabs to each other.

5. A brace for the ankle joint according to claim 1, wherein said outer cover further comprises a reinforcement portion made of cloth for locking an adjacent heel.

6. A brace for the ankle joint according to claim 5, wherein said reinforcement portion comprises an inelastic material affixed to the inner surface of the outer cover by means such as sewing, and located so that, when the brace is applied to the ankle joint, the reinforcement portion contacts an area extending from a sole of an adjacent foot to a portion corresponding to the Achilles tendon via a portion below the ankle joint.

7. A brace for the ankle joint according to claim 1, wherein said connection plates are made of a semi-rigid material.

8. A brace for the ankle joint according to claim 1, wherein said guard members comprise a semi-rigid material having curved inner surfaces corresponding generally to the shapes of the inner and outer sides of a lower leg adjacent to the ankle joint and define holes at locations corresponding to the ankle joint.

9. A brace for the ankle joint according to claim 8, wherein each of said guard members further comprises a padding layer located on the curved inner surface thereof.

10. A brace for the ankle joint according to claim 1 further comprising third attaching means detachably attaching the guard members to the inner surface of said outer cover to prevent said guard members from getting out of position.

* * * * *